United States Patent
Buck et al.

[11] Patent Number: 6,007,498
[45] Date of Patent: Dec. 28, 1999

[54] METHOD AND APPARATUS FOR COLLECTING VAGINAL FLUID AND EXFOLIATED VAGINAL CELLS FOR DIAGNOSTIC PURPOSES

[75] Inventors: Robert L. Buck, Lake Oswego; William H. Fleming, Hillsboro, both of Oreg.

[73] Assignee: A.FEM Medical Corporation, Portland, Oreg.

[21] Appl. No.: 09/036,742

[22] Filed: Mar. 9, 1998

Related U.S. Application Data

[63] Continuation of application No. 08/651,048, May 17, 1996, abandoned.

[51] Int. Cl.[6] .................................................. A61B 10/00
[52] U.S. Cl. ............................................................ 600/572
[58] Field of Search .................................. 600/572, 573, 600/574; 604/327, 328, 330

[56] References Cited

U.S. PATENT DOCUMENTS

| | | |
|---|---|---|
| 2,566,190 | 8/1951 | Greiner et al. . |
| 2,905,169 | 9/1959 | Nieburgs . |
| 3,547,930 | 12/1970 | Blomqvist et al. . |
| 3,726,277 | 4/1973 | Hirschman . |
| 3,815,580 | 6/1974 | Oster . |
| 3,850,160 | 11/1974 | Denson . |
| 3,983,873 | 10/1976 | Hirschman . |
| 4,095,542 | 6/1978 | Hirschman . |
| 4,142,476 | 3/1979 | Hirschman . |
| 4,175,561 | 11/1979 | Hirschman . |
| 4,196,562 | 4/1980 | Hirschman . |
| 4,294,253 | 10/1981 | Friese . |
| 4,595,392 | 6/1986 | Johnson et al. . |
| 4,627,849 | 12/1986 | Walton et al. . |
| 4,648,867 | 3/1987 | Conner et al. . |
| 4,743,237 | 5/1988 | Sweere . |
| 4,788,985 | 12/1988 | Manning et al. . |
| 4,944,734 | 7/1990 | Wallach . |
| 4,945,921 | 8/1990 | Okimoto . |
| 4,995,150 | 2/1991 | Gerstenberger et al. . |
| 4,999,417 | 3/1991 | Domb . |
| 5,073,202 | 12/1991 | Wallach . |
| 5,160,331 | 11/1992 | Forester et al. . |
| 5,163,931 | 11/1992 | Aldrett . |
| 5,190,533 | 3/1993 | Blackburn . |
| 5,256,477 | 10/1993 | Mahoney . |
| 5,415,994 | 5/1995 | Imrich et al. . |
| 5,542,914 | 8/1996 | Van Iten . |
| 5,571,540 | 11/1996 | Weyenberg et al. . |

FOREIGN PATENT DOCUMENTS 0 610 951   8/1994   European Pat. Off. .

OTHER PUBLICATIONS

A drawing from Puget Plastics Corporation with a hand-written heading "Device of Freund (Microbyx)", Apr. 10, 1995.

"Cytological Evaluation of Smears Prepared by the Tampon Method for the Detection of Carcinoma of the Uterine Cervix", by George N. Papanicolaou, M.D., pp. 1185–1190, Nov. 1954, vol. 7, No. 6, Cancer.

(List continued on next page.)

*Primary Examiner*—Cary O'Connor
*Assistant Examiner*—Pamela L. Wingood
*Attorney, Agent, or Firm*—Carter & Schnedler, P.A.

[57] ABSTRACT

There is provided a method and apparatus for collecting vaginal fluid and exfoliated vaginal cells for medical diagnostic purposes. An absorbent media is placed interlabially or intravaginally. Fluid is collected within the absorbent media. The absorbent media is removed, and the fluid is extracted therefrom. For intravaginal collection, the absorbent media may be placed in a housing having fluid receiving apertures therein. Medical diagnostic testing is performed on the extracted fluid.

14 Claims, 4 Drawing Sheets

OTHER PUBLICATIONS

"The Papanicolaou test for Cervical Cancer Detection, a Triumph and a Tragedy", by Leopold G. Koss, M.D., pp. 737–743, Feb. 3, 1989, vol. 261, No. 5, *The Journal of the American Medical Association*.

"Appraisal of a Newly Developed Self–Collection Device for Obtaining Cervical Specimens", by Masayoshi Noguchi, M.D., Masami Nakanishi, M.D., and Katsuya Kato, M.D., pp. 633–635, Sep.–Oct., 1982, vol. 26, No. 5, *Acta Cytologica*.

"Evaluation of a New Tampon Device for Cytologic Autocollection and Mass Screening of Cervical Cancer and its Precursors", by Arnold Bernstein, M.D., Saud Vitner, M.D., and Joe M. Webber, M.D., pp. 351–355, Feb. 1, 1985, vol. 151, No. 3, *American Journal of Obstetrics and Gynecology*.

"A Method for Mass Screening for Cytological Detection of Carcinoma of the Cervix Uteri", by Alexander Brunschwig, M.D., pp. 1182–1184, Nov. 1954, vol. 7, No. 6, *Cancer*.

"Fourth Decennial Review—Cell and Tissue Culture International Conference: Molecular Mechanisms in the Regulation of Cell Behavior", convened by the Tissue Culture Association, Hersey, PA, Sep. 22–26, 1986, Memorandum dated Aug. 11, 1986 from Vincent J. Cristofalo, Program Chairman.

"Detection of Endometrial Adenocarcinoma by Tampon–Smear Method", by Alexander Brunschwig, M.D. with comments by George N. Papanicolaou, M.D., pp. 120–123, Jan.–Feb. 1957, vol. 10, No. 1, *Cancer*.

"A Method for the Collection and Examination of the Exfoliative Cytology of the Human Female Reproductive Tract from Menstrual Blood Flow", by Matthew Freund, Ph.D. and Alexander Sedlis, M.D., pp. 497–500, Jul.–Aug. 1977, vol. 21, No. 4, *Acta Cytologica*.

"The Normal Exfoliative Cytology of Menstrual Blood", by Margaret L. Couture, B.S., Matthew Freund, Ph.D., and Alexander Sedlis, M.D., pp. 85–89, Jan.–Feb. 1979, vol. 23, No. 1, *Acta Cytologica*.

"Diagnostic Value and Potential of Menstrual Blood Flow for the collection and Examination of the Exfoliative Cytology of the Human Female Reproductive Tract", by Matthew J. Freund, Ph.D. and Margaret Couture, B.S., Proc. 26th Annual AOA/NOF Research Conference, JOAO, 82:142, 1982.

"The Presence of Endocervical Cells in the Exfoliative Cytology of Menstrual Blood", by Margaret L. Couture, B.S. and Matthew J. Freund, Ph.D., pp. 827–832, 1983, vol. 48, *Cytologia*.

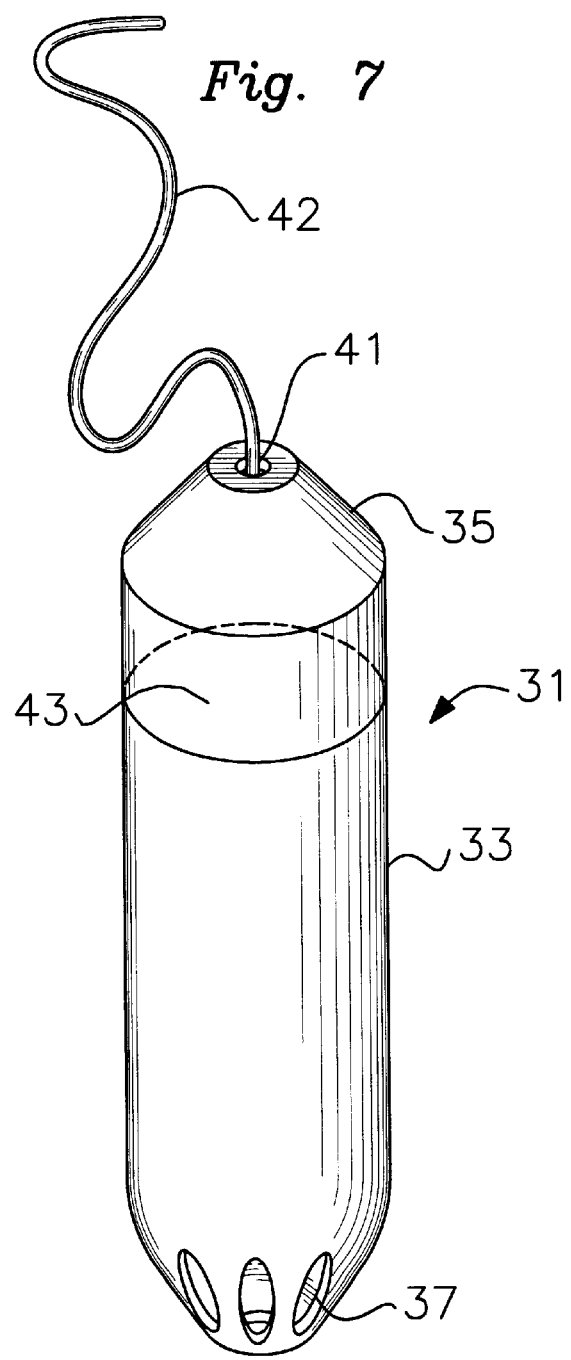
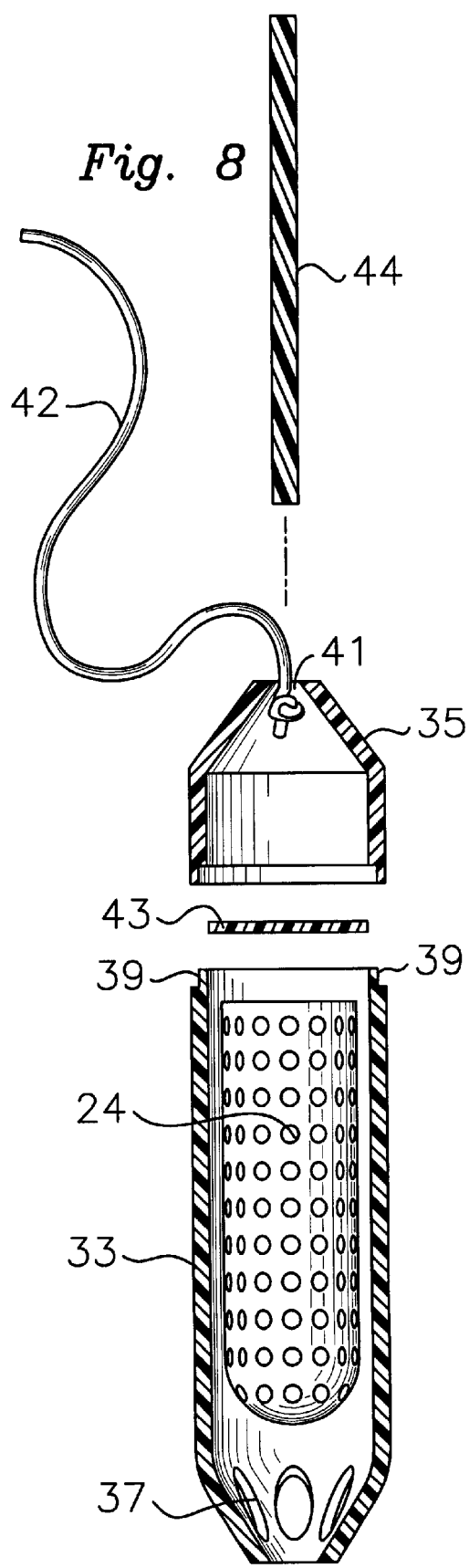

METHOD AND APPARATUS FOR COLLECTING VAGINAL FLUID AND EXFOLIATED VAGINAL CELLS FOR DIAGNOSTIC PURPOSES

This application is a continuation of application No. 08/651,048, filed May 17, 1996, abandoned.

BACKGROUND OF THE INVENTION

This invention relates to medical diagnostic testing.

More particularly, it relates to the collection of vaginal fluids and exfoliated vaginal cells for diagnostic purposes.

Currently, the vast majority of clinical diagnostic testing of biological fluids utilize serum and urine. It is believed that the United States Food and Drug Administration has not approved a clinical diagnostic test which utilizes any biological fluid other than whole blood, serum, plasma, saliva or urine. Tears and sweat are other fluids being used for various non-FDA approved diagnostic purposes, although such uses have been very limited. These fluids are very different in composition and their uses in clinical medicine.

The use of gynecological tissue for cancer diagnostic purposes has been limited to the traditional PAP Test Cervical Scraping (PTCS method of collection) and the subsequent histological smears for cervical cancer screening. A chemical or immunochemical analysis of non-menstrual vaginal fluid, menstrual fluid and/or the cellular extracts of menstrual fluid for the purpose of disease detection or patient well-being have not been exploited by the general medical community.

There have been a number of articles written by Dr. Matthew Freund and others which suggest that one may collect a large quantity of cervical and endometrial cells from menstrual fluids rather than through the traditional PTCS method. Dr. Freund found that both ectocervical and other cells collected from the menstrual fluid flow are well preserved for standard laboratory cytological procedures. They are similar in appearance to cells collected by current clinical methods, and give similar reactions to chemicals and stains, and may be analyzed by the same procedures as cervical smears for PAP testing.

OBJECTS OF THE INVENTION

It is therefore one object of this invention to provide an improved method for collecting vaginal fluid and vaginal cells for diagnostic purposes.

It is another object of this invention to provide a non-invasive method for collecting vaginal fluid and vaginal cells for diagnostic purposes.

It is still another object of this invention to provide an over-the-counter kit for collecting vaginal fluid and vaginal cells for diagnostic purposes.

SUMMARY OF THE INVENTION

In accordance with one form of this invention, there is provided a method for collecting vaginal fluid and exfoliated vaginal cells in menstrual fluid for medical diagnostic purposes. An absorbent media is placed interlabially or intravaginally. Fluid is collected within the absorbent media. The absorbent media is removed, and the fluid is extracted therefrom. For intravaginal collection, the absorbent media may be placed in a housing having fluid receiving apertures prior to insertion into the vagina. Medical diagnostic testing is performed on the extracted fluid.

Preferably the absorbent media used to collect vaginal fluid is an interlabia pad, such as the pads described in U.S. Pat. Nos. 3,726,277; 3,983,873; and 4,196,562 issued to Hirschman and licensed to Athena Medical Corporation, assignee of the present invention, or the pad described in U.S. Pat. No. 4,995,150 issued to Gerstenberger et al and assigned to Athena Medical Corporation. The Hirschman and Gerstenberger et al patents hereby are incorporated herein by reference.

It is preferred that the absorbent media used to collect exfoliated vaginal cells from menstrual fluid be of a shape similar to a tampon, but of a different construction and composition. Preferably, the tampon shaped device includes an absorbent core which is at least partially surrounded by a porous matrix.

Over-the-counter kits may be provided so that the collection of the fluids may be done by the consumer in the privacy of her home.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIG. 7 is a pictorial view of a housing for the fluid collection device shown in FIG. 1;

FIG. 8 is an exploded partial sectional view of the housing of FIG. 7.

DESCRIPTION OF THE PREFERRED EMBODIMENTS

Vaginal fluid and vaginal cells originating from intravaginal secretions, such as menstrual fluid, can be used to monitor several important clinical parameters, including cervical cancer, candida, chlamydia, trichomonas, bacterial vaginosis, i.e. gardnerella, and the sexually transmitted diseases, including HIV, syphilis, gonorrhea, human papilloma virus, and herpes infections. In addition, the fluid extract can be useful in measuring certain metabolic clinical parameters that have traditionally been limited to blood collections. Such parameters can be glucose, cholesterol, pituitary hormones, thyroid hormones, steroid hormones, therapeutic drugs, drugs of abuse, nutritional markers (prealbumin, etc.), fetal disease markers during pregnancy (placental protein markers) and levels of certain unknown metabolites that may be characterized by immunochemical (ELISA, RIA, FPIA, EMIT) or physical (NMR, HPLC, HPCE, HPTLC, GC-MS or FTIR) diagnostic techniques.

The fluid collection apparatus of the subject invention may be an interlabia pad constructed in accordance with U.S. Pat. Nos. 3,726,277 and 3,983,873 issued to Hirschman. The pad is formed from a fluid absorbent material, preferably rayon, which has better properties for sample collection than compacted cellulose, which is used in tampons. Other natural or synthetic fibers with similar hydrodynamic properties to rayon could be used. The pad is adapted to be inserted into the interlabia space by the user for absorbing vaginal discharges. The pad is securely retained in place despite substantial increases in its weight due to the absorption of vaginal fluids. The pad has been found to be safe and extremely comfortable for the user and is non-invasive.

Figure 1:
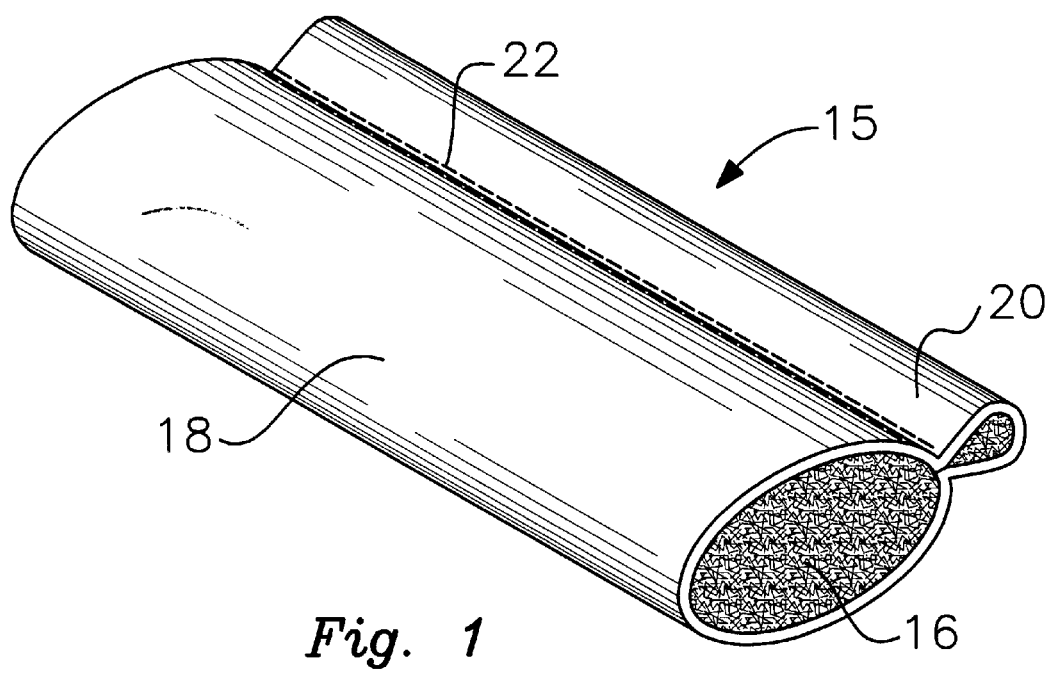
FIG. 1 is a pictorial view of a fluid collection device which may be used in accordance with this invention and is particularly useful in the collection of vaginal fluid.

Referring now more particularly to FIG. 1, there is provided interlabia pad 15 which includes an absorbent inner rope 16 covered by outer covering 18. The absorbent inner rope 16 may be made of the same absorbent material referred to above. A portion 20 of covering 18 extends along the side rope 16 so as to provide a place for the user to grip the pad for insertion into and withdrawal from the interlabia space. Preferably opposing sides of the cover are sewn or ultrasonically sealed together, depending on the type of material, as indicated along attachment line 22. The pad of FIG. 1 is more fully described in U.S. Pat. No. 4,196,562 issued to Hirschman. It has been found that the pad shown in FIG. 1 is useful in collecting vaginal fluids for diagnostic purposes.

Figure 2:
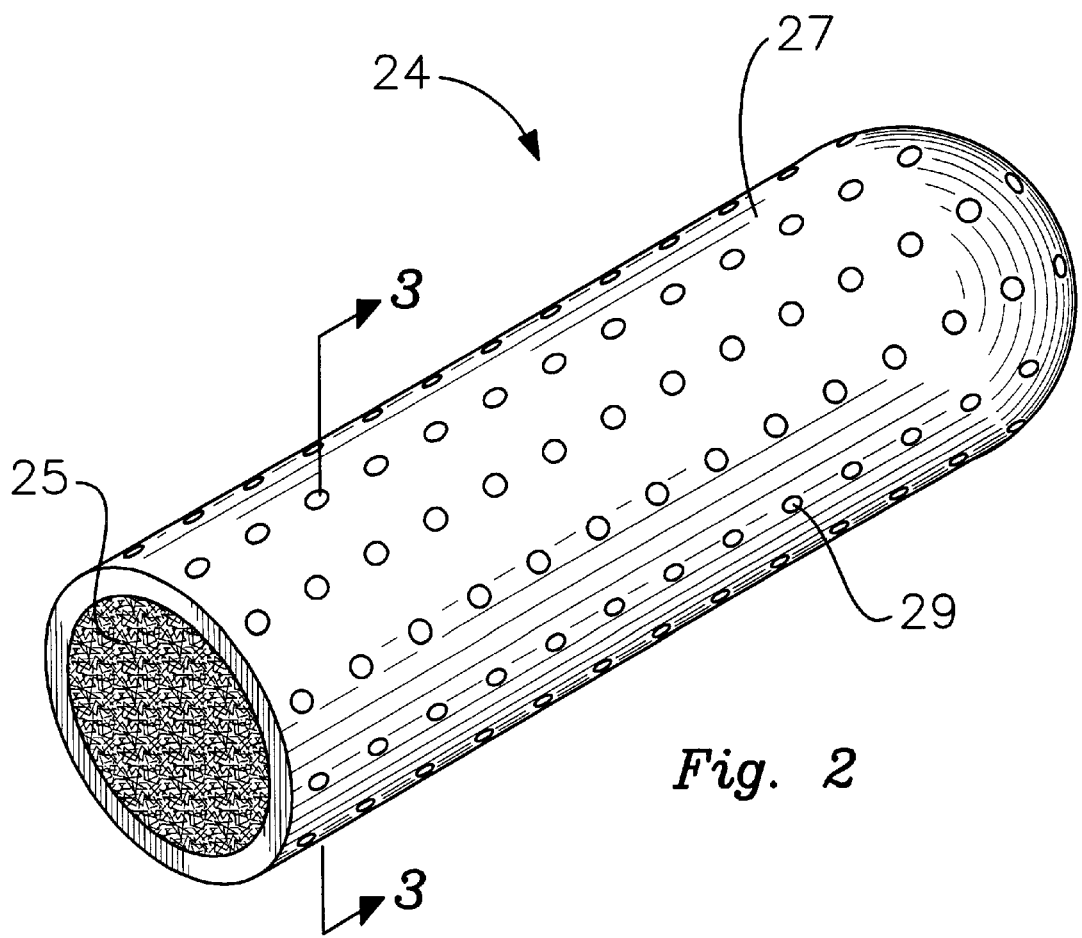
FIG. 2 is a pictorial view of a fluid collection device which may be used in accordance with this invention and is particularly useful in the collection of vaginal cells from menstrual fluid.
Figure 3:
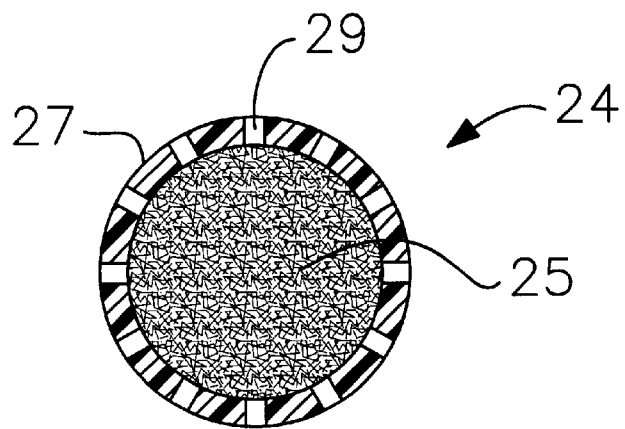
FIG. 3 is a sectional view of the device of FIG. 2.
Figure 4:
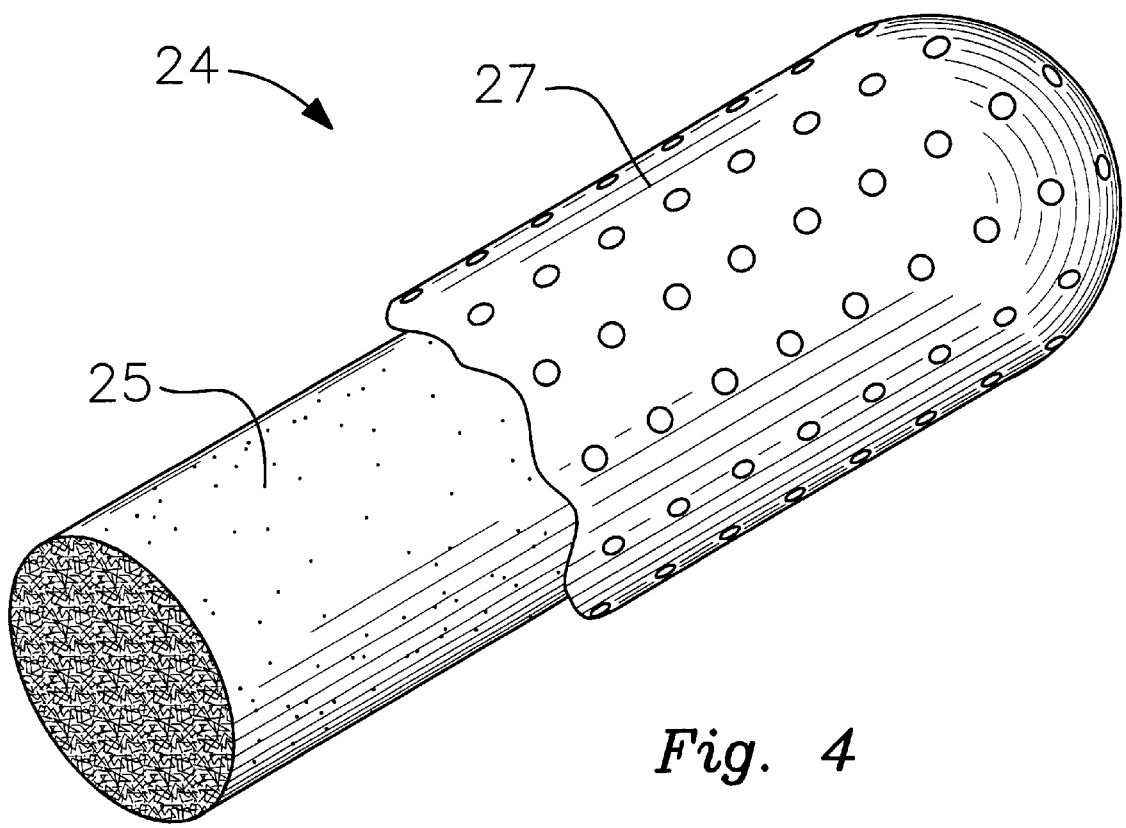
FIG. 4 is a partial pictorial view of the device of FIG. 2 with a portion of the outer matrix removed.

FIGS. 2, 3 and 4 show absorbent device 24 which is shaped like a tampon, but has a different structure and function. Absorbent device 24 includes a soft inner core 25 made of a fluid absorbent material made of a highly absorbent, but extractable, material, such as rayon, cellulose, cotton or other natural or synthetic fibers. Core 25 is able to absorb at least five times its weight in fluid. Preferably, core 25 is made of rayon fibers to eliminate dehydration and trapping of cellular elements, which occur to a greater extent with compacted cellulose materials employed in tampons. Device 24 includes an outer covering 27 to enhance its stability and to permit fluid to freely pass therethrough into core 25. Covering 27 is made of a highly porous material, such as sponge or nylon, and includes a matrix of pores 29 which allows for the collection of cellular debris without dehydration or inversible trapping within the matrix. The porous matrix allows for a greater ease of extraction and high quality of cellular material obtained. Device 24 is inserted intravaginally, in close proximity to the cervix.

Device 24 is also useful as a vaginal fluid collection device, particularly, for collecting blood and fluid from menstrual flow.

In cases where the fluid is to be collected intravaginally, the absorbent device 15 or 24 may be inserted into an elongated housing having a plurality of fluid receiving apertures therein. This may be seen better in reference to FIGS. 7 and 8. Elongated housing 31 includes a lower hollow portion 33 and an upper hollow portion 35. The lower portion 33 includes a plurality of apertures 37 for permitting fluid to enter the inside of the housing. The inside of the housing receives absorbent device 15 or 24. The upper portion of the housing 35 is in the form of a cap. The cap is removably secured to the lower portion of the housing 33 by engagement with studs 39. The housing with the absorbent material 24 received therein is inserted into the vagina for collecting fluids. Once the fluids are collected, the housing is removed from the vagina, using pull string 42. Opening 41 is provided in the top of the cap. A rod or plunger 44 may be placed into opening 41 and pressed against plate or disc 43 within device 24 to compress the fluid laden absorbent device and thus, squeeze out the fluids. The fluids will flow back through apertures 37 and into a collection vessel.

Figure 5:
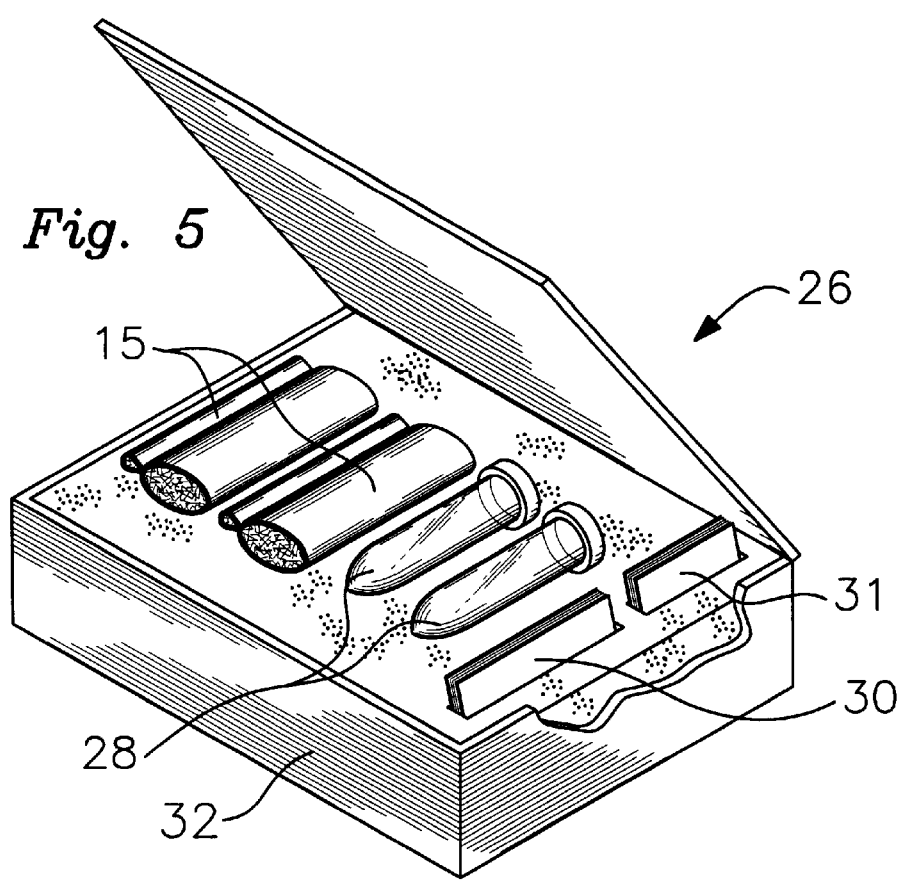
FIG. 5 is a pictorial view of a collection kit in accordance with the present invention.

The pads 15 are preferably included as a part of a vaginal fluid collection kit 26, as shown in FIG. 5, containing shipping tubes 28, mailing labels 30 and instructions 32, all housed in box 33. Housing 33 may also be included in the kit. Kit 26 is preferably available over-the-counter or from a physician and may be conveniently used by the consumer in the privacy of her home. The pad is first inserted interlabially and remains inserted for a specified amount of time. When ready, the pad is dropped into a disposable sample container 28 containing extraction/preservative solution and is mailed to a laboratory for analysis. Thus there is provided a non-invasive, simple, convenient and private sample collection procedure which allows collection of vaginal fluids using the kit, with its attendant advantages over having to go to a physician's office or clinic for a cervical scrape, or for blood collection.

Figure 6:
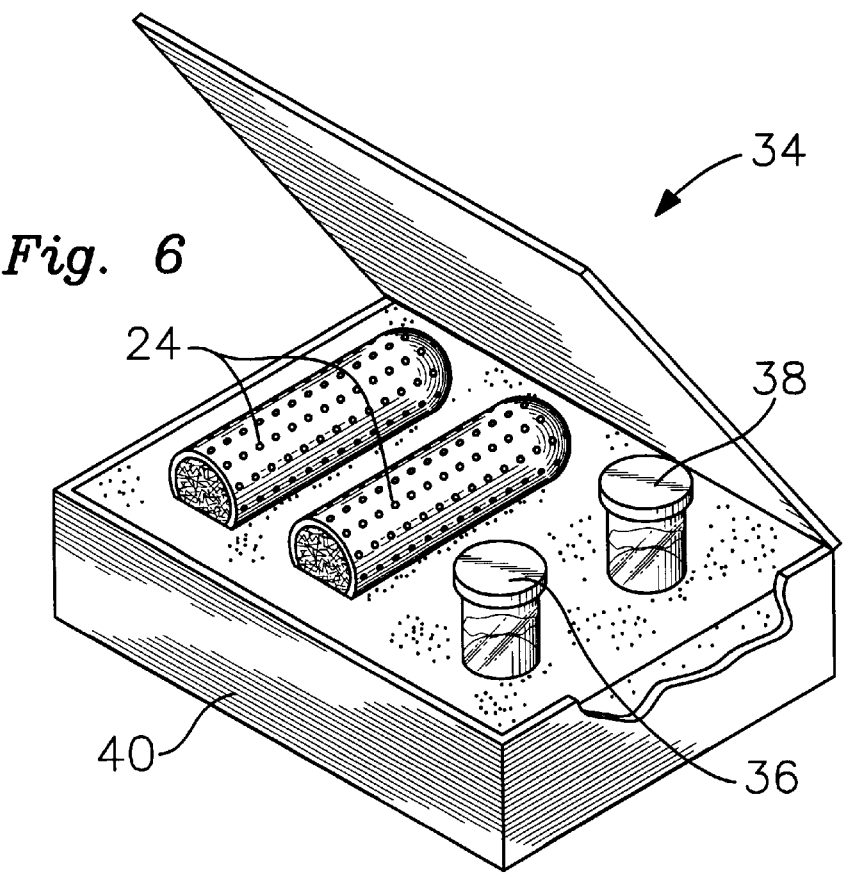
FIG. 6 is a pictorial view of another collection kit in accordance with the present invention.

Device 24 is particularly adapted to collect exfoliated cells or other specimen materials from vaginal fluid. Device 24 is also preferably included in an exfoliated cell collection kit 34, as shown in FIG. 6. Kit 34 includes device 24 and sample vials 36 and 38, containing an extraction buffer and/or preservative solution. The top of the sample vial is sealable. Device 24 and cups are received in box 40. Device 24 is inserted into the vaginal tract or labia and allowed to collect/absorb for short periods or overnight. Device 24 is then removed by the user and placed in sample vial 36 containing the extraction buffer and preservative. The vial containing the specimen is then sealed and mailed to a testing laboratory. This technique is also a non-invasive, convenient, simple and private method of sample collection. It is believed that the quantity of cells collected is greater and the collection is more consistent than that for the PTCS method. Use of the extraction buffer, preservative buffer, or both will vary depending on the types of test desired. Additional material needed for mailing of biohazardous material may be added to the kit. Instructions which contain a patient information sheet to be filled out by the user to be mailed with the sample may also be added to the kit.

Both the PTCS and blood collection methods require a trained health professional to collect the samples and do not offer the advantages of privacy and non-invasiveness, as set forth above. In addition, when used for cervical cancer detection, the quality of cells obtained by the method of this invention is comparable to or greater than that of the PTCS for diagnosing cervical cancer. Furthermore, it is believed that the consistency of the sample collection is inherently superior using teachings of this invention over PTCS. The PTCS method can vary significantly in quality and quantity due to technique variations between health care technicians and the anatomical differences among patients. These variations in sample collection using the PTCS method are believed to be the main reason for the high false negative rate among cervical cancer tests. The method of this invention does not rely on technique dependent procedures to obtain a representative sample, and as such, is less likely to allow a false negative test to occur. In addition, the fluid sample contains certain cellular molecular components, i.e. hemoglobin, that can be measured and then used as internal qualitative markers to address sample adequacy and standardization issues.

Thus there is provided a simple, inexpensive and convenient method for the collection of vaginal fluid and vaginal cells for diagnostic purposes. The method is non-invasive and kits may be purchased by the consumer over the counter, resulting in far less expense and inconvenience to the consumer. In addition, it is believed that the diagnostic accuracy will be greatly enhanced, particularly for cervical cancer detection.

From the foregoing description of the preferred embodiments of the invention, it will be apparent that many modifications may be made therein. It will be understood, however, that these embodiments of the invention are exemplifications of the invention only and that the invention is not limited thereto. It is to be understood therefore that it is intended in the appended claims to cover all modifications that fall within the true spirit and scope of the invention.

We claim:

1. A method for collecting vaginal fluid and/or exfoliated vaginal cells contained in the fluid for diagnostic purposes comprising the steps of:

placing a fluid absorbent media in the interlabial space;

collecting fluid in the absorbent media while said absorbent media is located in the interlabial space; retaining said absorbent media in the interlabial space for a sufficient time to collect a sufficient amount of fluid for diagnostic purposes;

removing the absorbent media;

extracting fluid from the absorbent media;

performing medical diagnostic testing on the extracted fluid.

2. A method as set forth in claim 1, wherein said fluid absorbent media is in the form of an interlabia pad.

3. A method as set forth in claim 2, wherein said interlabia pad includes a major portion and a minor portion and wherein said fluid absorbent media is removed by gripping said minor portion and removing said interlabia pad.

4. A method as set forth in claim 1, wherein said absorbent media includes an absorbent inner rope and an outer covering.

5. A method as set forth in claim 1, wherein the extracted fluid contains cells, including ectocervical, cervical, endometrial, vaginal and blood cells.

6. A method as set forth in claim 1, wherein the diagnostic testing is directed to abnormal cells associated with cancers, including cervical, endometrial and vaginal.

7. A method as set forth in claim 1, wherein the diagnostic testing is directed to organisms and biological material associated with bacterial, viral and parasitic diseases.

8. A method as set forth in claim 7, wherein said bacterial, viral and parasitic diseases include gonorrhea, syphilis, trichomonas, chlamydia, candida, papillomavirus, herpes, gardenerella and acquired immunodeficiency syndrome.

9. A method as set forth in claim 1, wherein the diagnostic testing is directed to biological materials associated with cancers.

10. A method as set forth in claim 1, further including the step of placing said absorbent media in a liquid extraction medium, wherein said liquid extraction medium contains preservatives and buffers.

11. A method as set forth in claim 1, further including the step of placing said absorbent media into a shipping container prior to extracting fluid from said absorbent media.

12. A method as set forth in claim 1, wherein said diagnostic testing is immunochemical.

13. A method as set forth in claim 1, wherein said diagnostic testing is a physical diagnostic technique.

14. A method for collecting cells contained in vaginal fluid for diagnostic purposes comprising the steps of:

placing a fluid absorbent media in the interlabial space;

collecting fluid containing cells in the absorbent media while said absorbent media is located in the interlabial space; retaining said absorbent media in the interlabial space for a sufficient time to collect a sufficient amount of fluid for diagnostic purposes;

removing the absorbent media;

extracting fluid from the absorbent media;

performing medical diagnostic testing on the cells.

* * * * *